(12) United States Patent
Gallenkamp et al.

(10) Patent No.: US 10,457,651 B2
(45) Date of Patent: Oct. 29, 2019

(54) METHOD FOR PRODUCING 3-ALKYLSULFANYL-2-CHLORO-N-(1-ALKYL-1H-TETRAZOL-5-YL)-4-TRIFLUOROMETHYL-BENZAMIDES

(71) Applicant: Bayer CropScience Aktiengesellschaft, Monheim am Rhein (DE)

(72) Inventors: Daniel Gallenkamp, Wuppertal (DE); Mark James Ford, Wiesbaden-Breckenheim (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 16/342,280

(22) PCT Filed: Oct. 16, 2017

(86) PCT No.: PCT/EP2017/076307
§ 371 (c)(1),
(2) Date: Apr. 16, 2019

(87) PCT Pub. No.: WO2018/073157
PCT Pub. Date: Apr. 26, 2018

(65) Prior Publication Data
US 2019/0233382 A1    Aug. 1, 2019

(30) Foreign Application Priority Data

Oct. 20, 2016 (EP) .................... 16194840

(51) Int. Cl.
*C07D 257/06* (2006.01)
*C07C 323/09* (2006.01)
*C07C 323/62* (2006.01)

(52) U.S. Cl.
CPC .......... *C07D 257/06* (2013.01); *C07C 323/09* (2013.01); *C07C 323/62* (2013.01)

(58) Field of Classification Search
CPC .... C07D 257/06; C07C 323/09; C07C 323/62
See application file for complete search history.

(56) References Cited

U.S. PATENT DOCUMENTS

| | | |
|---|---|---|
| 8,114,816 B2 | 2/2012 | Ahrens et al. |
| 8,481,749 B2 | 7/2013 | Braun et al. |
| 2010/0004129 A1 | 1/2010 | Ahrens et al. |
| 2012/0058892 A1 | 3/2012 | Braun et al. |
| 2018/0208563 A1 | 7/2018 | Ahrens et al. |

FOREIGN PATENT DOCUMENTS

| | | |
|---|---|---|
| EP | 3316687 A1 | 5/2018 |
| WO | 2009149806 A2 | 12/2009 |
| WO | 2012028579 A1 | 3/2012 |

OTHER PUBLICATIONS

Cramp et al., 1995, caplus an 1995:219090.*
Ishikawa et al., 2007, caplus an 2007:618412.*
Spangenberg et al., 2016, caplus an 2016:24611.*
International Search Report for PCT/EP2017/076307, dated Jan. 3, 2018.

* cited by examiner

*Primary Examiner* — Sun Jae Yoo
(74) *Attorney, Agent, or Firm* — McBee Moore Woodward & Vanik IP, LLC

(57) ABSTRACT

A method for preparing 3-alkylsulphanyl-2-chloro-N-(1-alkyl-1H-tetrazol-5-yl)-4-trifluoromethylbenzamides of the formula (I) is described.

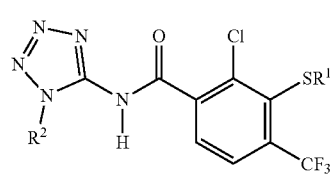

(I)

The substituents $R^1$ and $R^2$ therein are radicals such as alkyl and substituted phenyl.

14 Claims, No Drawings

METHOD FOR PRODUCING 3-ALKYLSULFANYL-2-CHLORO-N-(1-ALKYL-1H-TETRAZOL-5-YL)-4-TRIFLUOROMETHYL-BENZAMIDES

CROSS-REFERENCE TO RELATED APPLICATIONS

This application is a National Stage entry of International Application No. PCT/EP2017/076307, filed Oct. 16, 2017, which claims priority to European Patent Application No. 16194840.1, filed Oct. 20, 2016.

BACKGROUND

Field

The invention relates to a method for preparing 3-alkylsulphanyl-2-chloro-N-(1-alkyl-1H-tetrazol-5-yl)-4-trifluoromethylbenzamides which are used as agrochemically active substances. In particular, the invention relates to a method for preparing 2-chloro-3-methylsulphanyl-N-(1-methyl-1H-tetrazol-5-yl)-4-trifluoromethylbenzamide in its stable crystal modification.

Description of Related Art

Numerous agrochemically active N-(tetrazol-5-yl)arylcarboxamides are known from WO 2012/028579 A1. 3-Alkylsulphanyl-2-chloro-N-(1-alkyl-1H-tetrazol-5-yl)-4-trifluoromethylbenzamides have proven to be particularly advantageous. The 3-alkylsulphanyl-2-chloro-4-trifluoromethylbenzoic acids required for the preparation thereof may be prepared according to a method described in WO2009/149806 A1. However, this method cannot be used for a large-scale industrial synthesis due to the low yields and expensive starting materials. Moreover, in the case of the compound 2-chloro-3-(methylsulphanyl)-N-(1-methyl-1H-tetrazol-5-yl)-4-(trifluoromethyl) benzamide, the preparation according to a process described in WO 2012/028579 A1 does not lead to the stable crystal modification thereof, which has considerable application-related advantages, described WO 2017/005585 A1.

SUMMARY

An object of the present invention is to provide a method for preparing 3-alkylsulphanyl-2-chloro-N-(1-alkyl-1H-tetrazol-5-yl)-4-trifluoromethylbenzamides which overcomes the disadvantages of the methods known from the prior art.

It has now been found that 3-alkylsulphanyl-2-chloro-N-(1-alkyl-1H-tetrazol-5-yl)-4-trifluoromethylbenzamides may be prepared, starting form 2,3-dichlorobenzotrifluoride, by the reaction sequence of an alkylthiolation, carboxylation and subsequent amidation.

The present invention therefore relates to a method for preparing 3-alkylsulphanyl-2-chloro-N-(1-alkyl-1H-tetrazol-5-yl)-4-trifluoromethylbenzamides of the general formula (I), characterized in that a) in a first step 2,3-dichlorobenzotrifluoride (II) is reacted with a thiolate (IV) to give a 2-alkylsulphanyl-3-chlorobenzotrifluoride (III), b) in a second step the 2-alkysulphanyl-3-chlorobenzotrifluoride (III) is reacted with an organometallic reagent to give [2-chloro-3-(alkylsulphanyl)-4-(trifluoromethyl) phenyl] metal anion (V) and subsequently with a carboxylating reagent to give 3-alkylsulphanyl-2-chloro-4-trifluoromethylbenzoic acid (VI), and c) in a third step amidation with a 5-amino-1-alkyltetrazole (VII) is effected with an activator in the presence of a base and an acyl transfer reagent to give 3-alkylsulphanyl-2-chloro-N-(1-alkyl-1H-tetrazol-5-yl)-4-trifluoromethyl-benzamide (I):

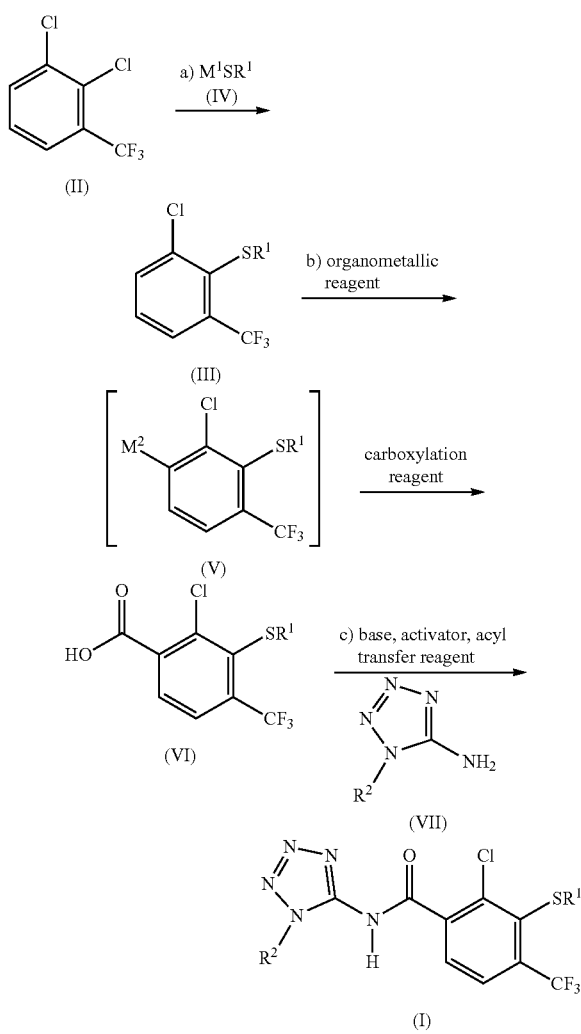

and d) where the substituents are as defined hereinbelow:

$R^1$ is $C_1$-$C_4$-alkyl or phenyl substituted by s radicals from the group consisting of chlorine, fluorine, methoxy and ethoxy, $R^2$ is $C_1$-$C_4$-alkyl or phenyl substituted by s radicals from the group consisting of chlorine, fluorine, methoxy and ethoxy, $M^1$ is lithium, sodium or potassium, $M^2$ is Li, ZnX, MgX, X is chlorine, bromine or iodine.

s is 0, 1, 2 or 3.

DETAILED DESCRIPTION OF A PREFERRED EMBODIMENT

Significant advantages of the method according to the invention are:

the use of readily obtainable starting materials,
the regioselective reaction in steps a) and b), the direct amidation of the benzoic acid without isolation of an intermediately formed benzoyl chloride.

the formation of the stable crystal modification at least for the case where R is methyl and the high overall yield.

In the formulae (I), (III), (IV), (V), (VI) and (VII), alkyl radicals having more than two carbon atoms may be straight-chain or branched. Alkyl radicals are e.g. methyl, ethyl, n- or isopropyl, n-, iso, t- or 2-butyl.

Preferably, $R^1$ and $R^2$ are $C_1$-$C_4$-alkyl, $M^1$ is sodium and $M^2$ is lithium. Particularly preferably, $R^1$ and $R^2$ are each methyl.

The starting materials used here are either commercially obtainable or accessible by simple methods known to those skilled in the art.

First Step of the Method According to the Invention:

Compound (IV) is used in a ratio from 1:1 to 2:1 mole equivalents, based on the compound of the general formula (II). Preference is given to a ratio from 1:1 to 1.5:1, particular preference being given to a ratio of 1.3:1. Typically, an aqueous solution of the compound (IV) is used. Particularly well-suited are sodium thiomethoxide (NaSMe) and potassium thiomethoxide (KSMe).

The compounds of the general formula (IV) may be prepared both in situ and ex situ from the corresponding thiols and a base such as carbonates, hydrogen carbonates, alkali metal hydroxides, alkaline earth metal hydroxides and organic bases. Suitable bases are LiOH, NaOH, KOH, $Ca(OH)_2$, $Na_2CO_3$, $K_2CO_3$, $Li_2CO_3$, $Cs_2CO_3$, $NaHCO_3$, $KHCO_3$, NaOAc, KOAc, LiOAc, NaOMe, NaOEt, NaO-t-Bu, Bu, KO-t-Bu, trialkylamines, alkylpyridines, phosphazenes and 1,8-diazabicyclo[5.4.0]undecene.

The reaction is generally conducted in an aqueous solution of the thiolate using a phase transfer catalyst without further solvent. The reaction can also be conducted in a solvent. Suitable solvents are ethers such as diethyl ether, diisopropyl ether, methyl t-butyl ether, THF, methyl-THF, dioxane, 1,2-dimethoxyethane, dimethoxyethane, diglyme or anisole; aromatic solvents such as toluene, xylene, chlorobenzene or 1,2-dichlorobenzene; aliphatic hydrocarbons such as n-hexane, n-heptane, cyclohexane or methylcyclohexane. Preference is given to methyl t-butyl ether, toluene, chlorobenzene, 1,2-dichlorobenzene, n-heptane or methylcyclohexane.

Phase transfer catalysts are ammonium or phosphonium salts such as methyltributylammonium chloride, methyltributylammonium bromide, methyltrioctylammnonium chloride, methyltrioctylammonium bromide, tetrahexylammonium chloride, tetrahexylammonium bromide, tetrahexylammonium iodide, tetraoctylammonium chloride, tetraoctylammonium bromide, tetraoctylammonium iodide, tributylhexadecylammonium chloride, tributylhexadecylammonium bromide, dimethyldidecylammonium chloride, dimethyldodecylbenzylammonium chloride, tetrabutylammonium chloride, tetrabutylammonium bromide, tetrabutylammonium hydrogen sulphate, benzyltributylammonium chloride, benzyltributylammonium bromide, Aliquat HTA-1®, Aliquat 134®, tributyltetradecylphosphonium chloride, tributyltetradecylphosphonium bromide, tributylhexadecylphosphonium bromide, tetraoctylphosphonium bromide, trihexyltetradecylphosphonium chloride, trihexyltetradecylphosphonium bromide. Preference is given to Aliquat 134® and tributyltetradecylphosphonium chloride. The phase transfer catalyst is used in a ratio from 0.1 to 10 mole per cent, based on the compound of the general formula (II). Preference is given to 1 to 6 mole per cent, particular preference being given to 2 to 4 mole per cent.

The reaction is preferably conducted at a temperature of 20 to 80° C., preferably 50 to 80° C., particularly preferably 70 to 80° C. The reaction generally goes to completion after 5 to 12 hours. The reaction can also be conducted at elevated or reduced pressure.

Second Step of the Method According to the Invention:

The compound of the formula (III) is initially charged in an inert aprotic solvent at low temperature, optionally with or without catalytic amounts of an amine. An alkyllithium compound as metallation reagent is then slowly metered in. After metered addition is complete, a transmetallation of the [2-chloro-3-(alkylsulphanyl)-4-(trifluoromethyl)phenyl] lithium compound initially formed can take place by addition of a corresponding metal salt at low temperature. The compounds of the general formula (V) are not isolated but are further reacted directly by addition of a carboxylation reagent. Here, the carboxylation reagent is metered in until an exothermic reaction is no longer apparent and the compound of the general formula (V) is converted fully to the compound of the general formula (VI).

Carbon dioxide, chloroformic esters or isocyanates may be used as carboxylation reagent for example. Preference is given to carbon dioxide.

The reaction is conducted under anhydrous conditions in an inert aprotic solvent. Suitable inert aprotic solvents are $C_5$-$C_8$ linear, branched or cyclic hydrocarbons such as pentane, hexane, cyclohexane, heptane, methylcyclohexane, isooctane and ethers such as tetrahydrofuran, 2-methyltetrahydrofuran, dioxane, diethyl ether, tert-butyl methyl ether, cyclopentyl methyl ether and glycol ethers. Preference is generally given to ethers and mixtures of hydrocarbons and ethers as solvent. Particular preference is given to mixtures of tetrahydrofuran and hydrocarbons.

Suitable metallation reagents are alkyllithium compounds or lithium amide compounds such as lithium diisopropylamide or lithium 2,2,6,6-tetramethylpiperidide, which function as a strong base. Preference is given to commercially available alkyl lithium compounds such as methyllithium, ethyllithium, isopropyllithium, n-butyllithium, isobutyllithium, sec-butyllithium, n-pentyllithium, neopentyllithium, n-hexyllithium and 2-(ethylhexl)lithium. Particular preference is given to n-butyllithium. The alkyllithium compound is used in a ratio from 0.9:1 to 1.2:1, based on the compound of the general formula (III). Preference is given to a ratio from 0.95:1 to 1.1:1, particular preference being given to a ratio of 1:1.

As metal salts, equimolar amounts of the corresponding zinc or magnesium halides may be used such as, for example, $ZnCl_2$, $ZnBr_2$, $MgCl_2$, $MgBr_2$ or $MgBr_2 \cdot OEt_2$. An advantage of transmetallation to $M^2$=ZnX, MgX is the increased stability of the corresponding [2-chloro-3-(alkylsulphanyl)-4-(trifluoromethyl)phenyl] metal compound at 0 to 23° C. in comparison to $M^2$=Li. In the case $M^2$=Zn, the reactivity towards electrophiles is significantly reduced whereby no reaction with carbon dioxide occurs.

By using catalytic amounts of an amine, the yield and purity of the compound of the general formula (VI) can be increased in comparison to the sole use of an alkyllithium compound. Suitable amines are primary or secondary amines such as n-propylamine, diethylamine, diisopropylamine or 2,2,6,6-tetramethylpiperidine. Preference is given to using diisopropylamine. The amine is used in a ratio from 0.1 to 20 mole per cent, based on the compound of the general formula (III). Preference is given to 0.1 to 10 mole per cent, particular preference being given to 5 to 10 mole per cent.

The reaction is generally conducted at a temperature of −60° C. to −80° C. By means of transmetallation to $M^2$=Zn or Mg, the compound of the general formula (V) may also be warmed to 0 to 23° C. without enhanced decomposition occurring.

Particular preference is given to the following combination from. the groups of the metallation reagents, solvents, amines and electrophiles described above: n-butyllithium, THF in combination with a $C_6$-$C_8$ hydrocarbon, diisopropylamine or 2,2,6,6-tetramethylpiperidine and carbon dioxide.

Third Step of the Method According to the Invention:

The compound of the formula (VI) is initially charged in a suitable solvent with an acyl transfer reagent of the general formula (VIII), a base and a 5-amino-2-alkyl-1H-tetrazole of the general formula (VII). An activating reagent (activator) is then slowly metered in and further stirred, optionally at elevated temperature.

The compounds of the formulae (VI) and (VII) are typically used in a molar ratio of 0.8 to 1.5. They are preferably used in equimolar amounts.

N1-substituted imidazoles of the general formula (VIII) may be used as acyl transfer reagent.

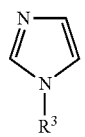

(VIII)

$R^3$ therein is $C_1$-$C_{12}$-alkyl or phenyl. $R^3$ is preferably methyl. As an alternative, 4-N,N-dimethylaminopyridine, for example, may be used. The acyl transfer reagent of the formula (VIII) and the compound of the formula (VI) are typically used in a molar ratio of 0.5 to 10, preferably of 1 to 3, particularly preferably of 1 to 2. When using tributylamine as base, a molar ratio of 1.0 is particularly preferred. When using 3-picoline as base, a molar ratio of 2.0 is particularly preferred.

Aromatic amines such as pyridine or picolines and tertiary amines such as triethylamine, tributylamine or diisopropylethylamine are suitable as base. 3-Picoline or tributylamine are particularly suitable. The base is used in a ratio from 2:1 to 4:1 mole equivalents, based on the compound of (VI). Preference is given to a molar ratio from 2:1 to 3:1. When using 3-picoline as base, a ratio of 2.5:1 is particularly preferred. When using tributylamine as base, a ratio of 3:1 is particularly preferred. If the acyl transfer reagent of the formula (VIII) and the compound of the formula (VI) is used in a molar ratio of ≥4.5, addition of a base is not required.

Suitable activators are thionyl chloride, phosgene, diphosgene, mesyl chloride, $POCl_3$, $PCl_5$ and oxalyl chloride. Preference is given to using thionyl chloride or phosgene. Particular preference is given to using thionyl chloride. The activator is used in a ratio from 0.5:1 to 3:1 mole equivalents, based on the compound (VI). Preference is given to a ratio from 1:1 to 2:1, particular preference being given to a ratio from 1.2:1 to 1.9:1.

Suitable solvents are inert organic solvents, preferably aliphatic, alicyclic or aromatic hydrocarbons such as petroleum ether, hexane, heptane, cyclohexane, methylcyclohexane, benzene, toluene, xylene and decaline; halogenated hydrocarbons such as chlorobenzene, dichlorobenzene, dichloromethane, chloroform, tetrachloromethane, 1,2-dichloroethane and trichloroethane; ethers such as diethyl ether, diisopropyl ether, methyl tert-butyl ether, methyl tert-amyl ether, dioxane, THF, methyl-THF 1,2-dimethoxyethane, 1,2-diethoxyethane and anisole; ketones such as acetone and methyl isobutyl ketone; nitriles such as acetonitrile, propionitrile, n- or isobutyronitrile and benzonitrile; amides such as N,N-dimethylformamide; N,N-dimethylacetamide, N-methylformanilide, N-methylpyrrolidine and hexamethylphosphoramide; pyridines such as 2-methylpyridine, 3-methylpyridine, 4-methylpyridine, 2,3-dimethylpyridine, 2-methyl-5-ethylpyridine, 2,6-dimethylpyridine, 2,4-dimethylpyridine, 3,4-dimethylpyridine and 2,4,6-trimethylpyridine. THF, acetonitrile or 3-methylpyridine is preferably used as solvent. Particular preference is given to using acetonitrile.

The reaction is typically conducted at a temperature of −5° C. to 80° C. When using 3-methylpyridine as solvent, the reaction is preferably conducted at 0 to 25° C. and the reaction is complete generally after 10 to 20 hours. When using acetonitrile as solvent and tributylamine as base, the reaction is preferably conducted at 0 to 25° C. and the reaction is complete generally after 1 to 5 hours. When using acetonitrile as solvent and 3-methylpyridine as base, the reaction is preferably conducted at 60 to 80° C. and the reaction is complete generally after 4 to 8 hours.

The workup of the reaction is effected according to a method described in the examples.

Compounds of the formula (III) are novel and are very well-suited as starting material for the second step of the method according to the invention. The present invention therefore further provides compounds of the formula (III)

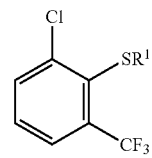

(III)

in which
$R^1$ is $C_1$-$C_4$-alkyl or phenyl substituted by s radicals from the group consisting of chlorine, fluorine, methoxy and ethoxy.
is 0, 1, 2 or 3.
$R^1$ is preferably $C_1$-$C_4$alkyl. $R^1$ is particularly preferably methyl.

Compounds of the formula (VI) are also novel and are very well-suited as starting material for the third step of the method according to the invention. The present invention therefore further provides compounds of the formula (VI)

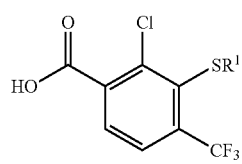

(VI)

in which
$R^1$ is $C_1$-$C_4$-alkyl or phenyl substituted by s radicals from the group consisting of chlorine, fluorine, methoxy and ethoxy,
s is 0, 1, 2 or 3.

R¹ is preferably $C_1$-$C_4$-alkyl. R¹ is particularly preferably methyl.

The following examples illustrate the invention in more detail without limiting it.

Preparation of 2-chloro-3-(methylsulphanyl)-N-(1-methyl-1H-tetrazol-5-yl)-4-(trifluoromethyl) benzamide Step 1: 3-chloro-2-(methylsulphanyl)benzotrifluoride 500.0 g (2.28 mol, 1.0 eq) of 2,3-dichlorotrifluoromethylbenzene and 50.0 g (0.06 mol, 2.5 mol %) of aqueous 50% CYPHOS® (tetradecyltri-n-butylphosphonium chloride) solution are initially charged under nitrogen and heated to 80° C. 990.0 g (2.96 mol, 1.3 eq) of 21% aqueous sodium thiomethoxide solution is metered in at 80° C. over 2 h and the mixture is fluffier stirred at 80° C. for 4 h. The organic phase is drained off and the aqueous phase is extracted with 300 ml of toluene. The combined organic phases are combined and concentrated at 40° C./50 mbar. The residue is distilled under a reduced pressure of 10 mbar. This gives 361 g of a colourless liquid (b.p. 104° C./10 mbar) in a yield of 70%. ¹H-NMR (CDCl3, 400 MHz) δ (ppm)=7.67 (dd, J=8.1, 1.3 Hz, 1H), 7.64 (dd, J=8.0, 1.3 Hz, 1H), 7.38 (td, J=8.0, 0.8 Hz, 1H), 2.42 (s, 3H).

Step 2: 2-Chloro-4-trifluoromethyl-3-methylsulphanyl-benzoic acid

A solution of 100.0 g (0.44 mol, 1.0 eq) of 1-chloro-2-(methylsulphanyl)-3-(trifluoromethyl)benzene and 4.5 g (0.04 mol, 0.1 eq) of diisopropylamine are initially charged in 500 ml of THF under nitrogen and the mixture is cooled to −70° C. 122.3 g (0.44 mol, 1.0 eq) of 23% n-butyllithium solution in hexane is metered in at −70° C. over a period of 3 h and the mixture is then stirred for 2 h at −70° C. This gives an orange-red suspension. $CO_2$ gas is then introduced into the flask above the reaction solution such that the temperature does not exceed −60° C. After ca. 1 h, exothermicity is no longer apparent, and the reaction mixture is warmed to 23° C. over 1 h. This gives a cream-coloured suspension. 500 ml of methylcyclohexane are added and the mixture is then concentrated starting at 40° C./400 mbar up to 40° C./150 mbar. 500 ml of water are added to the pale yellow suspension and the mixture is stirred at 23° C. for 10 min, wherein the solid goes into solution. The organic phase is removed and discarded. 100 ml of 20% HCl are metered in to the aqueous phase (pH=1-2) over 1 h. The colourless solid is filtered off, washed with 350 ml of warm water at 40° C. and dried at 10 mbar/40° C. This gives 99.3 g of product (81% yield).

¹H-NMR (DMSO-$d_6$, 400 MHz) δ (ppm)=14.02 (s br, 1H), 7.88 (d, J=8.3 Hz, 1H), 7.85 (d, J=8.1 Hz, 1H), 2.42 (s, 3H).

Step 3: 2-chloro-3-(methylsulphanyl)-N-(1-methyl-1H-tetrazol-5-yl)-4-(trifluoromethyl)benzamide A solution of 100.0 g of 2-chloro-3-(methylsulphanyl)-4-(trifluoromethyl)benzoic acid (0.362 mol, 1.0 eq), 84.3 g of 3-picoline (0.905 mol, 2.5 eq), 59.5 g of 1-methyl-1H-imidazole (0.724 mol, 2.0 eq) and 41.5 g of 5-amino-1-methyl-1H-tetrazole (95%, 0,398 mol, 1.1 eq) are initially charged in 640 ml of acetonitrile under nitrogen and the mixture is heated to reflux. 68.9 g of thionyl chloride (0.579 mol, 1.6 eq) are metered in over 3 h. Subsequently, the mixture is stirred at 74° C. for 3 h. Then ca. 80-90% of the acetonitrile is distilled off at 40° C./50 mbar up to a residual weight of ca. 350-400 g. 400 ml of 10% HCl are metered in at 23° C. over 5h and the mixture is then stirred at 23° C. for 1 h. The beige-coloured, solid is filtered off, washed successively with 500 ml of 10% HCl and 400 ml of water and subsequently dried at 40° C./10 mbar. This gives 124 g of the stable crystal modification in a yield of 95%.

¹H-NMR (CDCl3, 400 MHz) δ (ppm)=11.25 (s br, 1H), 7.80 (d, J=8.3 Hz, 1H), 7.73 (d, J=8.1 Hz, 1H), 4.15 (s, 3H), 2.45 (s, 3H).

The invention claimed is:

1. Method for preparing 3-alkylsulphanyl-2-chloro-N-(1-alkyl-1H-tetrazol-5-yl)-4-trifluoromethylbenzamides of the general formula (I), comprising reacting 2,3-dichlorobenzotrifluoride (II) with a thiolate (IV) to give a 2-alkysulphanyl-3-chlorobenzotrifluoride (III), b) reacting the 2-alkysulphanyl-3-chlorobenzotrifluoride (III) with an organometallic reagent to give [2-chloro-3-(alkylsulphanyl)-4-(trifluoromethyl) phenyl] metal anion (V) and subsequently with a carboxylating reagent to give 3-alkylsulphanyl-2-chloro-4-trifluoromethylbenzoic acid (VI), and c) effecting amidation with a 5-amino-1-alkyltetrazole (VII) with an activator in the presence of a base and an acyl transfer reagent to give 3-alkylsulphanyl-2-chloro-N-(1-alkyl-1H-tetrazol-5-yl)-4-trifluoromethylbenzamide (I):

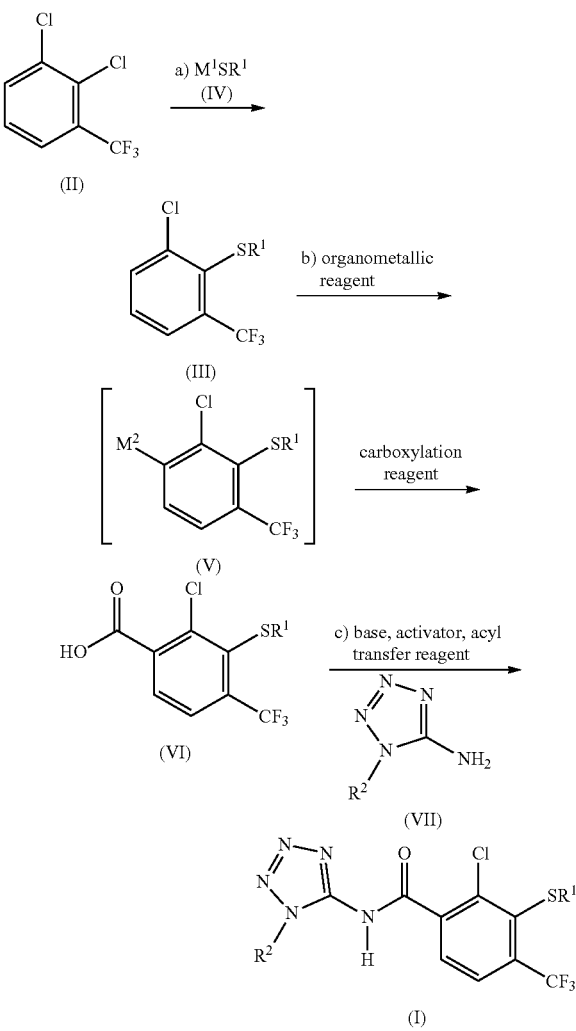

and d) where the substituents are as defined hereinbelow:

R¹ is $C_1$-$C_4$-alkyl or phenyl substituted by s radicals selected from the group consisting of chlorine, fluorine, methoxy and ethoxy, $R^2$ is $C_1$-$C_4$-alkyl or phenyl substituted by s radicals selected from the group consisting of chlorine, fluorine, methoxy and ethoxy, $M^1$ is lithium, sodium or potassium, $M^2$ is Li, ZnX, MgX, X is chlorine, bromine or iodine, s is 0, 1, 2 or 3.

2. Method according to claim 1, wherein the thiolate (IV) used is NaSMe or KSMe.

3. Method according to claim 1, where $R^1$ is $C_1$-$C_4$-alkyl.

4. Method according to claim 1, wherein $R^1$ is methyl.

5. Method according to any claim 1, wherein $M^1$ is sodium.

6. Method according to claim 1, wherein $R^2$ is methyl.

7. Method according to claim 1, wherein the organometallic reagent used is an alkyllithium compound.

8. Method according to claim 1, wherein the carboxylating reagent used is carbon dioxide.

9. Method according to claim 1, wherein the activator used is thionyl chloride.

10. Method according claim 1, wherein the acyl transfer reagent used is 1-methyl-1H-imidazole.

11. Compound of formula (III), in which

(III)

$R^1$ is $C_1$-$C_4$-alkyl or phenyl substituted by s radicals selected from the group consisting of chlorine, fluorine, methoxy and ethoxy, and s is 0, 1, 2 or 3.

12. Compound of formula (III) according to claim 11, where $R^1$ is methyl.

13. Compound of formula (VI) in which $R^1$ is $C_1$-$C_4$-alkyl or phenyl substituted by s radicals from the group consisting of chlorine, fluorine, methoxy and ethoxy, and s is 0, 1, 2 or 3

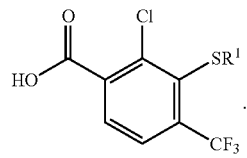

(VI)

14. Compound of formula (VI) according to claim 13, where $R^1$ is methyl.

* * * * *